(12) United States Patent
Termanini et al.

(10) Patent No.: US 10,188,407 B2
(45) Date of Patent: Jan. 29, 2019

(54) DRILL GUIDE FOR ACETABULAR CUP FASTENERS

(71) Applicant: HIP INNOVATION TECHNOLOGY, LLC., Boca Raton, FL (US)

(72) Inventors: Zafer Termanini, Port Saint Lucie, FL (US); Steven MacDonald, London (CA); Brian Vanhiel, Smyrna, GA (US); Linda Braddon, Canton, GA (US)

(73) Assignee: HIP INNOVATION TECHNOLOGY, LLC, Boca Raton, FL (US)

( * ) Notice: Subject to any disclaimer, the term of this patent is extended or adjusted under 35 U.S.C. 154(b) by 0 days.

(21) Appl. No.: 15/742,238

(22) PCT Filed: Jul. 15, 2016

(86) PCT No.: PCT/US2016/042436
§ 371 (c)(1),
(2) Date: Jan. 5, 2018

(87) PCT Pub. No.: WO2017/019328
PCT Pub. Date: Feb. 2, 2017

(65) Prior Publication Data
US 2018/0214164 A1    Aug. 2, 2018

Related U.S. Application Data

(60) Provisional application No. 62/197,207, filed on Jul. 27, 2015.

(51) Int. Cl.
*A61B 17/17*    (2006.01)
*A61F 2/34*    (2006.01)
(Continued)

(52) U.S. Cl.
CPC ...... *A61B 17/1746* (2013.01); *A61B 17/8872* (2013.01); *A61F 2/34* (2013.01);
(Continued)

(58) Field of Classification Search
CPC .................................................. A61B 17/1746
See application file for complete search history.

(56) References Cited

U.S. PATENT DOCUMENTS

| 4,428,374 A | 1/1984 | Auburn |
| 5,928,287 A * | 7/1999 | Keller .................. A61F 2/4609 |
|  |  | 606/91 |

(Continued)

FOREIGN PATENT DOCUMENTS

DE        102011050019 A1    10/2012

OTHER PUBLICATIONS

International Search Report for corresponding application PCT/US2016/042436 dated Sep. 27, 2016.
(Continued)

*Primary Examiner* — Andrew Yang
(74) *Attorney, Agent, or Firm* — Norris McLaughlin PA (57) ABSTRACT

When an acetabular cup used in hip replacement surgery is to be affixed to the acetabulum using screws, the drill guide instruments of the invention are used to position a drill bit so that the screw holes drilled in the acetabulum are properly placed for optimum implantation of the acetabular cup. The drill guide is locked into the acetabular cup by spring loaded pins which position the guide over holes in the cup which accommodate the screws. The guide is used to position the drill bits and allow drilling. After drilling the guide is removed.

8 Claims, 7 Drawing Sheets

(51) Int. Cl.
*A61B 17/88* (2006.01)
*A61F 2/46* (2006.01)
(52) U.S. Cl.
CPC .... *A61F 2/4609* (2013.01); *A61F 2002/3404* (2013.01); *A61F 2002/3453* (2013.01)

(56) References Cited

U.S. PATENT DOCUMENTS

| | | |
|---|---|---|
| 7,727,282 B2 | 6/2010 | Slone et al. |
| 2009/0177239 A1* | 7/2009 | Castro ................ A61B 17/1728 606/86 B |
| 2012/0016485 A1 | 1/2012 | Sharp |
| 2015/0127113 A1 | 5/2015 | Termanini |

OTHER PUBLICATIONS

Written Opinion of the International Searching Authority for corresponding application PCT/US2016/042436 dated Sep. 27, 2016.

* cited by examiner

DRILL GUIDE FOR ACETABULAR CUP FASTENERS

This is an application filed under 35 USC 371 based on PCT/US2016/042436 filed 15 Jul. 2016, which in turn claims priority to U.S. Ser. No. 62/197,207 filed 27 Jul. 2015. The present application claims the full priority benefit of these prior applications and herein incorporates by reference the full disclosures of these prior applications as if set forth herein.

BACKGROUND OF THE INVENTION

Field of the Invention

The present invention relates to surgical instruments used to implant a hip prosthesis. More particularly, the invention has to do with a surgical tool system which comprises a drill guide, a handle and a drill bit used to drill screw holes in an acetabulum to implant an acetabular cup.

The Related Art

A reverse hip prosthesis is described in U.S. Pat. Nos. 8,313,531 B2 and 8,540,779 B2. The prosthesis and a revision surgery method also are described in U.S. Pat. No. 8,992,627 B2. The disclosures of these three patents are incorporated herein in their entireties by reference.

The present invention also relates to conventional hip prostheses which are well known in the art.

SUMMARY OF THE INVENTION

The acetabular cup can be affixed in the acetabulum with screws. The surgical tool system of the invention enables a surgeon to accurately drill holes at the proper angles and depths for optimum placement of the acetabular cup in the acetabulum. The system of the invention comprises a drill guide, a handle having a drill bit guide used in coordination with the drill guide and a drill bit.

DESCRIPTION OF THE PREFERRED EMBODIMENT

The surgical tool system of the invention is used for drilling holes in an acetabulum to accommodate or receive screws used to fasten an acetabular cup to the acetabulum. The acetabular cup in the first and second embodiments of the invention comprises a concave portion having a stem extending from the bottom thereof, slots disposed in the concave portion in close proximity to a circumferential edge of the acetabular cup and one or more through holes to accommodate screws for fastening the acetabular cup to the acetabulum. The first and second embodiments are for use with a reverse hip prosthesis. In the third embodiment, the tool system is used in connection with a conventional hip prosthesis which does not have a stem extending from the concave portion of the acetabular cup.

The surgical tool system comprises a drill guide sized to fit within the concave portion of the acetabular cup. Spring-loaded pins are arranged in the drill guide to engage the slots when the drill guide is optimally positioned within the acetabular cup. The drill guide also comprises one or more through holes sized and spaced to line up approximately concentrically with the through holes of the acetabular cup. A guide indent is provided for each hole, each guide indent being positioned on a beam member which traverses the drill guide at a circumferential edge thereof. A handle is provided comprising a shaft with a drill bit guide disposed at the distal end thereof. The drill bit guide has a drill bit guide distal end and a side portion. The drill bit guide is sized to engage a hole and the side portion is positioned to engage the guide indent for its respective hole. A drill bit is employed having a cutting portion and a shaft which is sized to pass through the drill bit guide.

The method of using the surgical tool system of the invention comprises the sequential steps of first placing the drill guide in an acetabular cup which has been positioned in an acetabulum. Then the drill guide is rotated within the cup until the pins engage the slots. A drill bit is then inserted into the drill bit guide before or after placing the distal end of the drill bit guide into a through hole and engaging the corresponding guide indent for the hole with the side portion of the drill bit guide. A hole is drilled into the acetabulum. Then the drill bit and drill bit guide are removed and a screw is inserted into the hole and tightened.

Referring to the drawings, the drill guide 1 illustrated in FIGS. 1-6 is comprised of a spherical base 2 having through holes 3 therein. The base 2 has a generally convex outer surface and a generally concave inner surface, the inner surface being designated by reference numeral 4 in FIG. 4. Disposed within and traversing the inner surface 4 is a beam 5 having pin slots 6 therein. The pin slots 6 accommodate pins 7 and each pin 7 has a pin handle 8.

Figure 1:
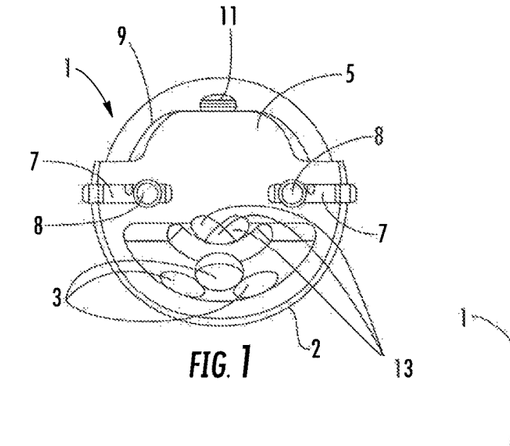
FIG. 1 is a top elevation view of a first embodiment of the drill guide of the invention.
Figure 2:
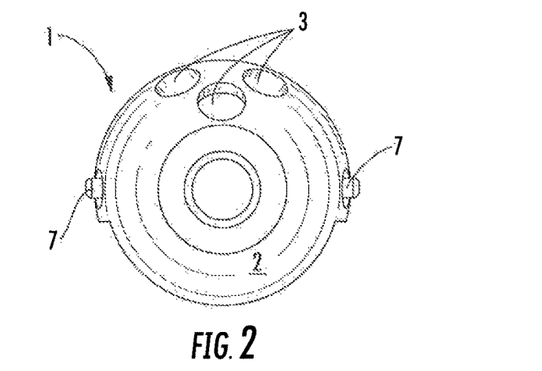
FIG. 2 is a bottom elevation view of the drill guide of FIG. 1.
Figure 3:
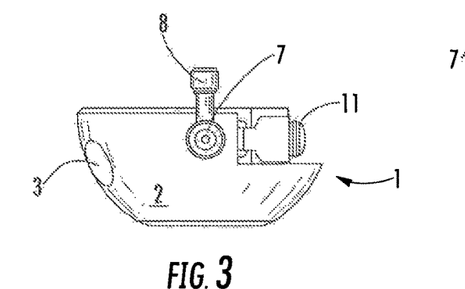
FIG. 3 is a side elevation view of the drill guide of FIG. 1.
Figure 4:
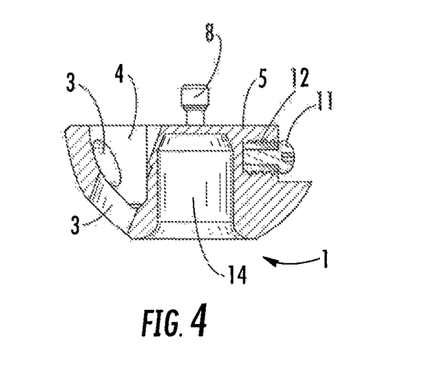
FIG. 4 is a section view of FIG. 3.
Figure 5:
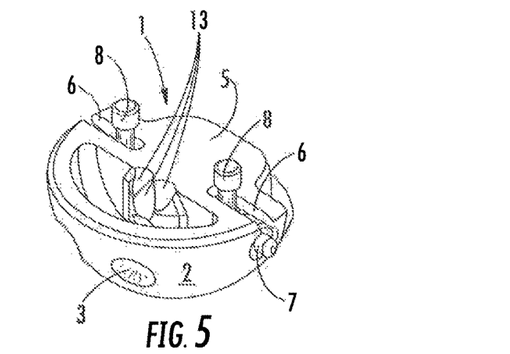
FIG. 5 is a perspective view of the first embodiment of the drill guide.
Figure 6:
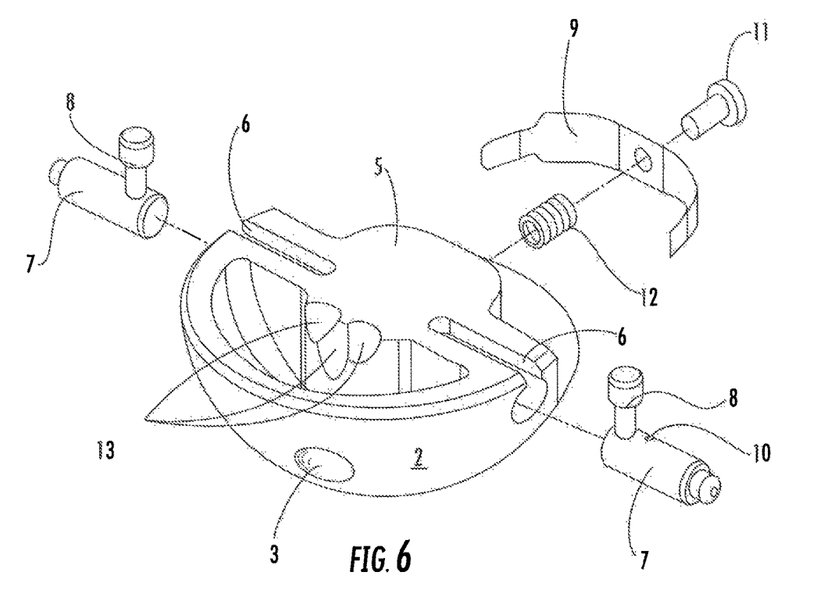
FIG. 6 is an exploded view of the first embodiment of the drill guide.

Referring to FIGS. 1 and 6, the pins 7 are urged in an outward direction by spring 9, the ends of which are disposed in spring slots 10. The spring 9 is secured to beam 5 by screw 11 and threaded bushing 12.

Figure 10:
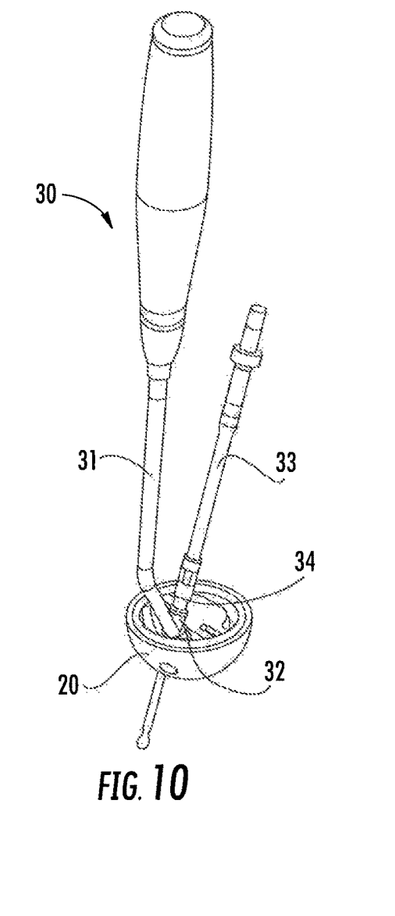
FIG. 10 is a perspective view of the surgical tools of the invention comprising a drill guide positioned in a reverse hip acetabular cup, a guide handle and a drill bit.
Figure 11:
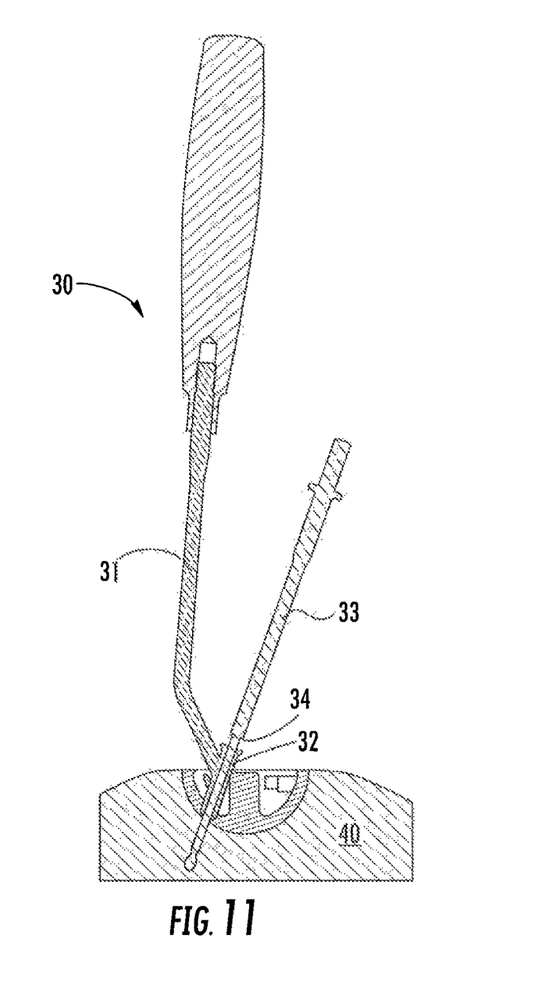
FIG. 11 is a section view of FIG. 10 with an added element to illustrate a portion of an acetabular bone.

Also disposed on beam 5 are guide indents 13. Each guide indent 13 is lined up with a hole 3 for the purpose of positioning guide handle 30 as illustrated in FIGS. 10 and 11. As will be understood by those having ordinary skill in the art, acetabular cups may have one hole for a screw or other fastener or they may have multiple holes, 10, 15, 20, etc. The drill guides of the present invention may be made for use with acetabular cups having any number of holes.

Figure 7:
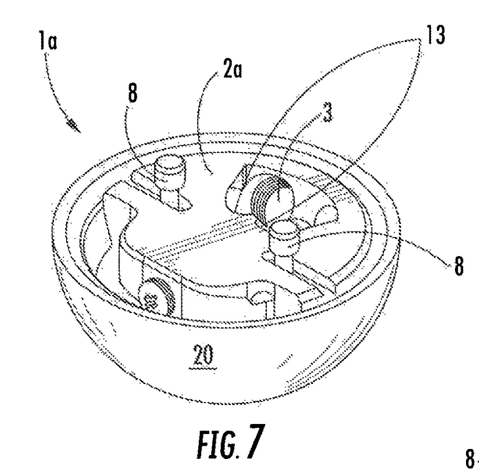
FIG. 7 is a perspective view of a second embodiment of a drill guide positioned in a reverse hip acetabular cup.
Figure 8:
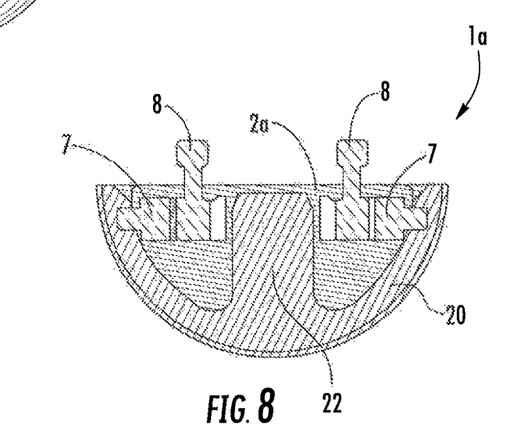
FIG. 8 is a section view of the drill guide of FIG. 7 positioned in a reverse hip acetabular cup.
Figure 9:
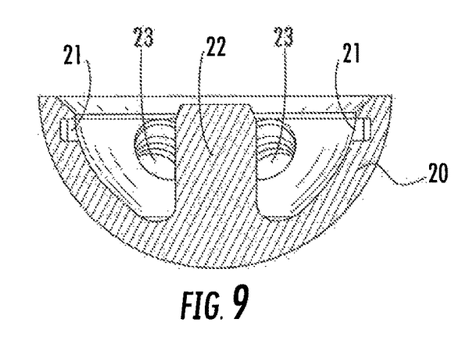
FIG. 9 is a section view of a reverse hip acetabular cup.

FIGS. 7 and 8 illustrate a second embodiment of a drill guide 1a positioned in reverse hip acetabular cup 20. This drill guide has all of the elements of the first embodiment illustrated in FIGS. 1-6 except that spherical base 2a is more filled in around guide indents 13. A section view of acetabular cup 20 without the drill guide is illustrated in FIG. 9. Acetabular cup 20 comprises cup slots 21, a stem 22 and cup holes 23, the cup holes being optionally threaded. As can be seen from FIGS. 4 and 8, the drill guides have an open shaft is sized to receive stem 22. Thus, the drill guides are sized to fit in the concave portion of acetabular cup 20.

The drill guide is placed in acetabular cup 20 after the acetabular cup 20 is positioned in the acetabulum 40. (See FIG. 11.) Placement of the drill guide in acetabular cup 20 is done by squeezing pin handles 8 towards one another, placing the drill guide into acetabular cup 20, releasing pin handles 8 and rotating the drill guide until pins 7 engage cup slots 21, thereby affixing the drill guide in position.

Referring to FIGS. 10 and 11, drill guide handle 30 is provided with a shaft 31 having a drill bit guide 32 disposed at the distal end thereof. The drill bit 33 has a stop 34 to prevent the drill from making a hole that is too deep. Drill bit 33 is placed in drill bit guide 32. The drill guide handle 30 is used by positioning the distal end of the drill bit guide 32 in a hole 3 (See also FIGS. 1-7.) of the drill guide and resting a side of the drill bit guide 32 on the appropriate guide indent 13. Of the three holes 3 and guide indents 13, the appropriate guide indent for the middle hole 3 is the middle guide indent 13. For the hole to the left of center, the guide indent to the left of center is used, etc. The drill bit 33 may be and preferably is placed in the drill bit guide 32 before the handle 30 positions the drill bit guide 32 in the drill guide. After each hole is drilled, the guide handle, bit and drill guide are removed, a screw is screwed in and tightened and the process is repeated for the second and third holes.

Figures 12, 12A, 13:
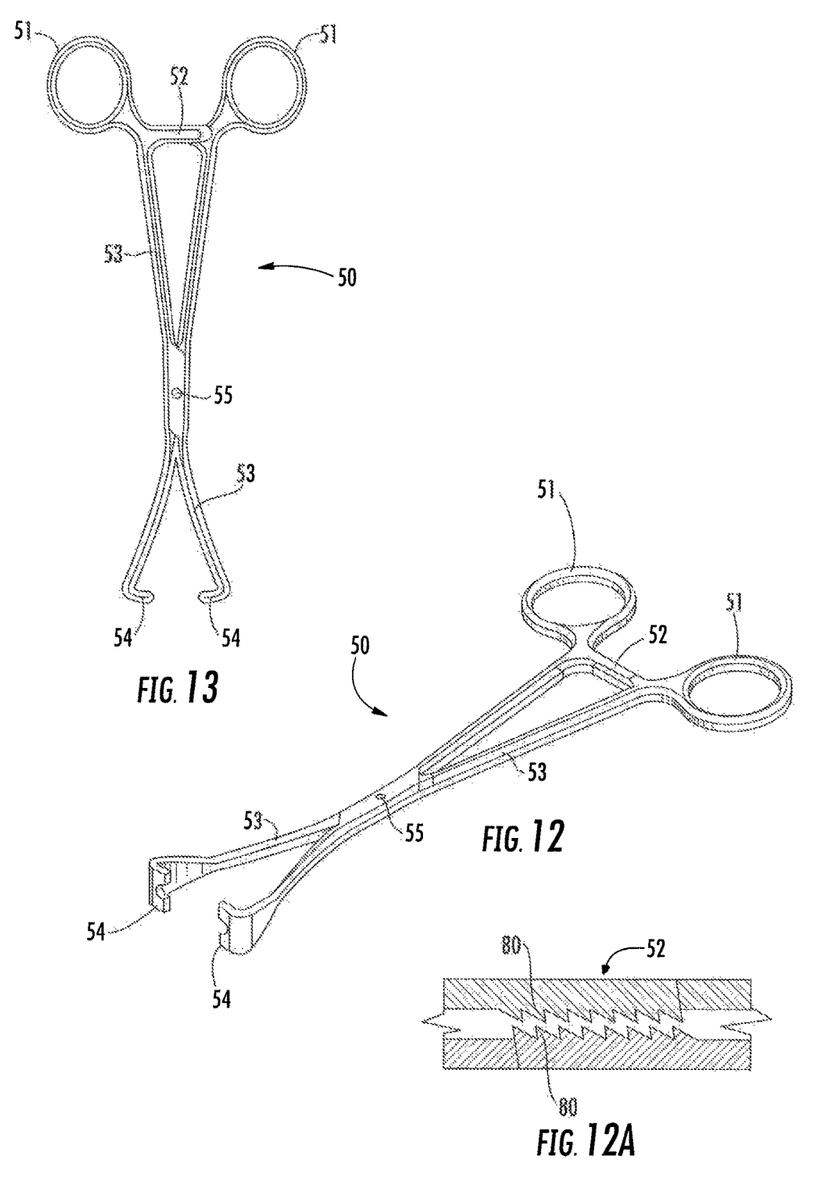
FIG. 12 is a perspective view of an insertion-removal tool which optionally can be used to insert the drill guide into an acetabular cup or remove it from the acetabular cup.
FIG. 12A is a side elevation view illustrating the ratcheting portion of the insertion removal tool.
FIG. 13 is an elevation view of the tool of FIG. 12.

Insertion-removal tool 50 is illustrated in FIGS. 12 and 13. The tool 50 is similar to a hemostat in size and construction. The tool comprises handles 51 at its proximal end and a ratcheting portion 52. As illustrated in FIG. 12A, ratcheting portion 52 has the same kind of teeth 80 as one would find in a hemostat. The ratcheting portion is releasable in the same manner as a hemostat. A pin 53 is positioned to provide leverage and grippers 54 are disposed at the distal end. The portion of the tool located between the pin 53 and grippers 54 may optionally be angled (for example at about 20°) (not shown).

Figure 14:
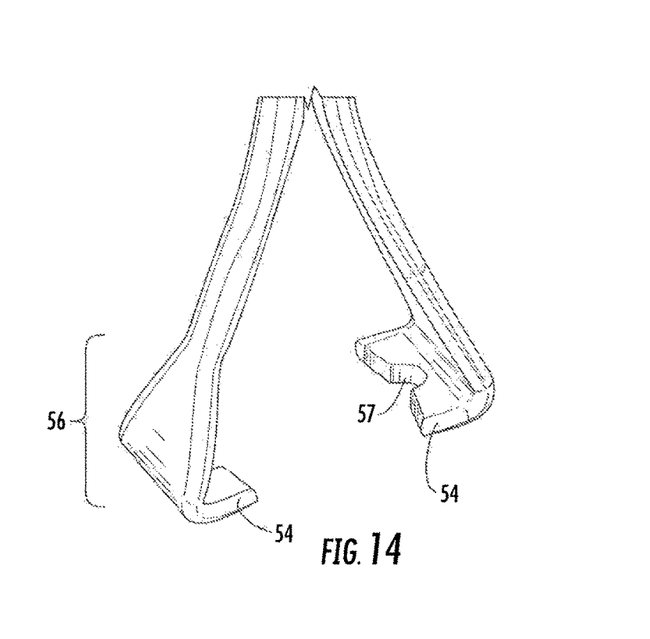
FIG. 14 is a magnified view of the distal end of the insertion-removal tool.
Figure 15:
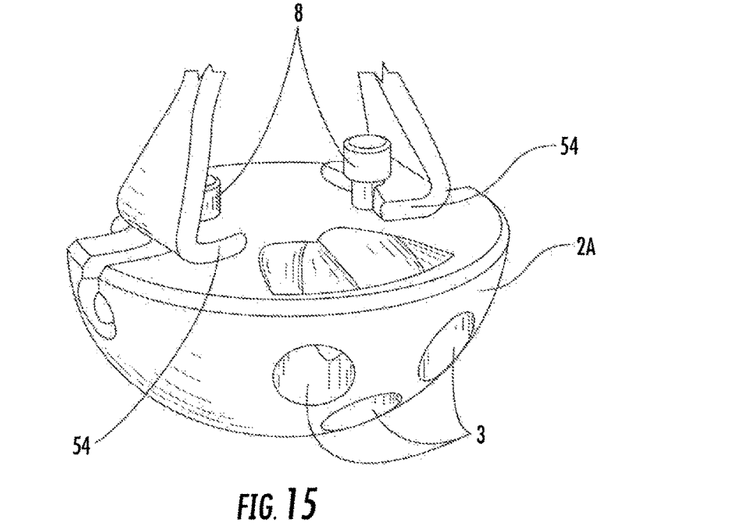
FIG. 15 illustrates the insertion-removal tool in use in connection with a drill guide.

A magnified view of the distal end of tool 50 is shown in FIG. 14, and FIG. 15 shows the tool in use. As illustrated, when tool 50 is used to insert or remove a drill guide into or out of an acetabular cup, the opposing notches 57 of grippers 54 at distal end 56 of tool 50 are placed in contact with pin handles 8 as shown. Using the tool 50, the pin handles 8 are squeezed toward one another so that the pins 7 recede and allow the drill guide to be inserted into or removed from an acetabular cup.

Figure 16:
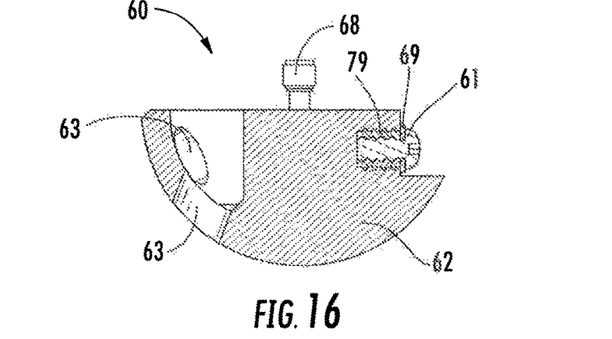
FIG. 16 is a section view of a third embodiment of a drill guide of the invention.
Figure 17:
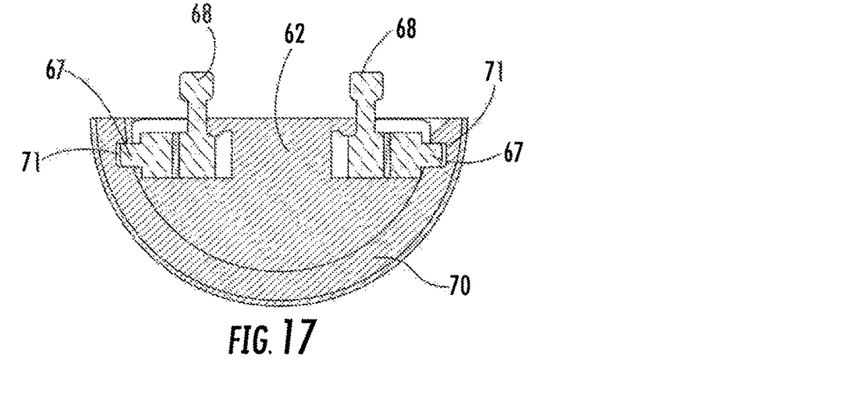
FIG. 17 is a section view of the drill guide of FIG. 16 positioned in a conventional acetabular cup.

A third embodiment of the drill guide of the invention is illustrated in section in FIG. 16 as drill guide 60. Drill guide 60 is used with a conventional acetabular cup 70 shown in section in FIG. 17. The drill guide 60 comprises a screw 61 which is threaded into threaded sleeve 79 and which secures a spring 69 to the drill guide in the same manner as screw 11 secures spring 9 to beam 5 as shown in FIGS. 1-6. Spring 69 is the same type of spring as spring 9. The drill guide 60 has a base 62, holes 63, pins 67 and pins 68, all of which function in the same manner as their counterparts in the first and second embodiments of the drill guides of the invention described herein. Conventional acetabular cup 70 also is provided with cup slots 71 which are engaged by pins 67.

The surgical instrument of the invention may be included within a kit which includes other tools and/or implant elements used in hip replacement surgery.

The invention claimed is:

1. A surgical tool system adapted for drilling holes in an acetabulum to accommodate screws used to fasten an acetabular cup to the acetabulum, the acetabular cup comprising a concave portion having a stem extending from the bottom thereof, cup slots disposed in the concave portion in close proximity to a circumferential edge of the acetabular cup and one or more through holes to accommodate screws for fastening the acetabular cup to the acetabulum, the surgical tool system comprising:

a drill guide sized to fit within the concave portion and having spring-loaded pins arranged to engage the cup slots when the drill guide is optimally positioned within the acetabular cup, the drill guide further comprising one or more through holes sized and spaced to line up approximately concentrically with the through holes of the acetabular cup and a guide indent for each hole, each guide indent being positioned on a beam member which traverses the drill guide at a circumferential edge thereof;

a handle comprising a shaft with a drill bit guide disposed at the distal end thereof, the drill bit guide having a drill bit guide distal end and a side portion, the drill bit guide being sized to engage a hole and the side portion being positioned to engage the guide indent for its respective hole; and a drill bit having a cutting portion and a shaft sized to pass through the drill bit guide.

2. A surgical tool system adapted for drilling holes in an acetabulum to accommodate screws used to fasten an acetabular cup to the acetabulum, the acetabular cup comprising a concave portion, cup slots disposed in the concave portion in close proximity to a circumferential edge of the acetabular cup and one or more through holes to accommodate screws for fastening the acetabular cup to the acetabulum, the surgical tool system comprising:

a drill guide sized to fit within the concave portion and having spring-loaded pins arranged to engage the cup slots when the drill guide is optimally positioned within the acetabular cup, the drill guide further comprising one or more through holes sized and spaced to line up approximately concentrically with the through holes of the acetabular cup and a guide indent for each hole, each guide indent being positioned on a beam member which traverses the drill guide at a circumferential edge thereof;

a handle comprising a shaft with a drill bit guide disposed at the distal end thereof, the drill bit guide having a drill bit guide distal end and a side portion, the drill bit guide being sized to engage a hole and the side portion being positioned to engage the guide indent for its respective hole; and a drill bit having a cutting portion and a shaft sized to pass through the drill bit guide.

3. A kit containing the surgical tool system of claim 1.

4. A method of using the surgical tool system of claim 1 comprising the sequential steps of:

placing the drill guide in an acetabular cup which has been positioned in an acetabulum and rotating the drill guide until the pins engage the cup slots;

inserting a drill bit into the drill bit guide, then placing the distal end of the drill bit guide into a through hole and engaging the corresponding guide indent for the hole with the side portion of the drill bit guide; and drilling a hole into the acetabulum, removing the drill bit and drill bit guide and inserting a screw into the hole and tightening the screw.

5. An insertion-removal tool adapted for inserting the drill guide of claim 1 into the acetabular cup and for removing the drill guide of claim 1 or 2 from the acetabular cup comprising:

two levers connected by and pivotable about a pivot pin, each lever having a proximal end and a distal end, the pin being disposed between the proximal and the distal end so that movement of the proximal ends towards one another will cause the distal ends to move toward one another; and a releaseable ratcheting portion disposed near the proximal end which prevents the levers from pivoting away from one another after they have been moved towards one another.

6. A kit containing the insertion-removal tool of claim 5.

7. A method of using the insertion-removal tool of claim 5 to insert a drill guide into an acetabular cup comprising the sequential steps of:

arranging each opposing notch on a spring-loaded pin; and engaging the spring-loaded pins by moving the handles toward one another and causing the spring-loaded pins to move inwardly until they do not project from the drill guide, locking the levers in position with the ratcheting portion, arranging the drill guide in the acetabular cup and rotating the drill guide into a position wherein the spring-loaded pins are lined up with the cup slots, then releasing the levers from the locked position allowing the pins to move into the cup slots and allowing removal of the insertion-removal tool from the drill guide.

8. A method of using the insertion-removal tool of claim 5 to remove a drill guide from an acetabular cup comprising the sequential steps of:

arranging each opposing notch on a spring-loaded pin; engaging the spring-loaded pins by moving the handles towards one another and causing the spring-loaded pins to move inwardly until they do not project from the drill guide, and locking the levers in position with the ratcheting portion and pulling the drill guide out of the acetabular cup.

* * * * *